United States Patent [19]

Sherman

[11] Patent Number: 5,562,921
[45] Date of Patent: Oct. 8, 1996

[54] STABLE SOLID PHARMACEUTICAL COMPOSITIONS CONTAINING ENALAPRIL MALEATE

[76] Inventor: Bernard C. Sherman, 50 Oldcolony Road, Willowdale, Ontario, Canada, M2L 2K1

[21] Appl. No.: 276,678

[22] Filed: Jul. 15, 1994

[51] Int. Cl.⁶ .............. A61K 9/20; A61K 38/00; A61K 31/70; A61K 31/715
[52] U.S. Cl. .............. 424/465; 514/19; 514/21; 514/23; 514/58; 514/558; 514/960
[58] Field of Search ............... 514/19, 21, 558, 514/23, 58, 960; 424/467, 468, 465

[56] References Cited

U.S. PATENT DOCUMENTS 4,374,829  2/1983  Harris et al. ............... 514/21
4,973,470  11/1990  Mills et al. ............... 424/467

FOREIGN PATENT DOCUMENTS 92119896  11/1992  European Pat. Off. .

OTHER PUBLICATIONS

*The Merck Index*, Tenth Edition (1983), p. 645, abstract no. 4352.

Primary Examiner—Kevin E. Weddington
Attorney, Agent, or Firm—Nixon & Vanderhye P.C.

[57] ABSTRACT

Enalapril maleate is unstable when associated with many excipients commonly used in the manufacture of pharmaceutical compositions. Stable solid compositions are provided by mixing enalapril maleate into a carrier that is comprised primarily of water-soluble carbohydrates and contains a lubricant other than magnesium stearate, a preferred lubricant being zinc stearate.

11 Claims, No Drawings

5,562,921

STABLE SOLID PHARMACEUTICAL COMPOSITIONS CONTAINING ENALAPRIL MALEATE

BACKGROUND OF THE INVENTION

U.S. Pat. No. 4,374,829 discloses the compound enalapril maleate, which is a drug useful to treat hypertension. This patent also discusses methods of formulating drugs into pharmaceutical compositions such as tablets and capsules.

In order to manufacture pharmaceutical tablets or capsules, it is necessary to mix the active ingredient with inactive ingredients which may serve as binders, fillers, disintegrating agents, lubricants, and colorants or have other purposes. Inactive ingredients are also known as 'excipients'. All of the inactive ingredients together (i.e., the totality of ingredients other than the active ingredient) are known as the 'carrier'.

After the active ingredient is mixed with the carrier, the mix is made into the tablets on a table press or filled into gelatin capsules on a capsule filling machine. The processes of preparing the mix and making tablets or filling capsules are well known to those skilled in the art of pharmaceutical formulation.

One of the requirements for an acceptable pharmaceutical composition is that it must be stable, so as not to exhibit substantial decomposition of the active ingredient during the time between manufacture of the composition and use by the patient.

Surprisingly, it has been found that enalapril maleate is not compatible with most of the usual excipients, including most of those mentioned in U.S. Pat. No. 4,374,829. Decomposition of enalapril maleate is accelerated by most of these excipients, thus making it very difficult to formulate a stable table or capsule containing enalapril maleate.

The difficulty of formulating a stable composition containing enalapril maleate is confirmed by European Patent Application No. 92119896.6. That application discloses that a stable formulation can be made by reacting enalapril maleate with a sodium compound to convert the enalapril maleate into enalapril sodium plus disodium maleate. Stability data contained in this patent application demonstrates that the final composition containing enalapril sodium mixed with disodium maleate and other ingredients is far more stable than a similar composition containing enalapril maleate.

However, the formulations of European Application No. 92119896.6 have the disadvantage of requiring the step of converting the enalapril maleate into enalapril sodium plus disodium maleate.

In light of the foregoing, the object of the invention is to enable production of a stable pharmaceutical table or capsule containing enalapril maleate.

SUMMARY OF THE INVENTION

It has been found that enalapril maleate is particularly unstable in the presence of microcrystalline cellulose and calcium phosphates, and also in the presence of magnesium stearate, which is the most commonly used lubricant.

A composition is provided in which the enalapril maleate is mixed into a carrier that omits ingredients which cause instability and is comprised primarily of water soluble carbohydrates. The carrier also contains a lubricant other than magnesium stearate, the preferred lubricant being zinc stearate.

DETAILED DESCRIPTION OF THE INVENTION

A solid pharmaceutical composition in the form of a tablet or capsule is made from a mix of the active ingredient (in this case, enalapril maleate) and a carrier. The carrier is a combination of excipients which will usually include the following:

i) a filler, to increase the weight and size of the composition to that desired.

ii) a disintegrant (i.e. disintegration agent), which is a substance that absorbs water and swells so as to cause the composition to absorb water and disintegrate in gastrointestinal fluid.

iii) a lubricant, to prevent sticking to the metal tooling used in the table compression or capsule filling process.

Other excipients may be present to serve as binders, colorants, glidants, or for other purposes.

There are many choices of excipients from which the formulator may choose to serve these purposes.

Specifications for many commonly used excipients are set out in the U.S. Pharmacopoeia and National Formulary, 1990 edition. Among excipients specified therein and useable as fillers are lactose anhydrous, lactose monohydrate, microcrystalline cellulose, starch, dibasic calcium phosphate, tribasic calcium phosphate, compressible sugar, dextrates, dextrose, dextrin, mannitol and sorbitol. Among excipients specified therein and used as disintegrants are microcrystalline cellulose, starch, croscarmellose sodium, sodium starch glycolate, and crospovidone. As will be noted from the foregoing, some excipients may serve as both fillers and disintegrants. Among excipients specified therein and used as lubricants are stearic acid and the magnesium, calcium and zinc salts of stearic acid. The most commonly used lubricant is magnesium stearate. Glyceryl monostearate, which is an ester of stearic acid, may also be used as a lubricant.

Iron oxides are often used as colorants, and colloidal sodium dioxide is often used as a glidant.

As aforesaid, one of the requirements for an acceptable pharmaceutical composition is that it must be sufficiently stable so as not to exhibit substantial decomposition of the active ingredient during the time between manufacture of the composition and use by the patient.

In the course of developing the within invention, many compositions in the form of tablets containing enalapril maleate were produced and tested for stability. Stability was tested by the technique known as accelerated stability testing. In such studies, samples are stored at elevated temperatures. This speeds decomposition and shortens the time needed to draw conclusions as to stability. At a temperature of 50° C., for example, decomposition that would take months at ambient temperature will occur within a few weeks. At the end of the desired test period, sample tablets are removed from the storage ovens and tested for extent of decomposition. The measurements of decomposition are usually done by high performance liquid chromatographic techniques, known as 'HPLC', which are well known to experienced pharmaceutical chemists.

In the course of the development work, tablets were initially made containing enalapril maleate along with lactose monohydrate, microcrystalline cellulose, starch, and magnesium stearate. It was found that after two weeks of storage of these tablets at 50° C., over ten percent of the enalapril maleate had decomposed, as indicated by the quantities of decomposition products measured by HPLC. When the experiments were repeated using microcrystalline cellulose and starch that had been well-dried to remove free water, the extent of decomposition was reduced to three or four percent, but this is still excessive.

Through extensive comparative experiments using various combinations of excipients, it was demonstrated that the presence of the microcrystalline cellulose, starch, and magnesium stearate all contributed to the decomposition.

Further comparative experiments enabled the following additional conclusions:

i) the use of the dibasic calcium phosphate or tribasic calcium phosphate as a filler also results in excessively rapid decomposition.

ii) there is little or no decomposition caused by use of various water-soluble carbohydrates as fillers, including specifically lactose anhydrous, lactose monohydrate, compressible sugar, dextrates, dextrose, dextrin, mannitol and sorbitol.

iii) the rate of decomposition is almost as high if magnesium stearate is replaced by calcium stearate. However, surprisingly, it was found that the rate of decomposition is substantially decreased, if any of stearic acid, zinc stearate or glyceryl monostearate is used as lubricant in place of magnesium stearate. Zinc stearate is a more efficient lubricant that either stearic acid or glyceryl monostearate, for preventing sticking to tooling. Hence zinc stearate is a preferred lubricant from the viewpoint of both stability and lubrication.

iv) The inclusion of any starch, croscarmellose sodium, crospovidone or sodium starch glycolate as disintegrant consistently gave higher rates of decomposition than when no disintegrant was used.

In order for a pharmaceutical table or capsule to be effective, it is necessary that the composition disintegrates or dissolves in gastrointestinal fluid after ingestion, so as to release the drug for absorption. It is for this reason that tablets or capsules will usually contain a disintegrant.

However, if the carrier is comprised primarily of substances that are water-soluble, the composition may dissolve sufficiently rapidly in gastrointestinal fluids so as not to require use of a disintegrant. Preferred compositions within the scope of the invention will not include a disintegrant.

For the purposes of this specification, water-soluble substances will be defined as substances that are sufficiently soluble in water such that tablets that are made from such substances and contain no disintegrant will dissolve in less than 1 hour in a disintegration test done as directed in the U.S. Pharmacopoeia and National Formulary.

In view of all the foregoing, compositions within the scope of the invention comprise enalapril maleate in a carrier having the following characteristics:

1. the carrier is substantially free of microcrystalline cellulose and calcium phosphates.

2. the carrier is comprised primarily of water-soluble substances.

3. the carrier is free or substantially free of magnesium stearate, and contains a lubricant other than magnesium stearate.

The carrier is also preferably free or substantially free of disintegrants. The water soluble substances are preferably carbohydrates, and preferably selected from lactose monohydrate, lactose anhydrous, dextrates, dextrose, dextrin, compressible sugar, mannitol and sorbitol. Most preferred is lactose monohydrate or lactose anhydrous. The lubricant will preferably be stearic acid, or a salt or ester of stearic acid other than magnesium stearate or calcium stearate. Most preferably, the lubricant will be zinc stearate.

EXAMPLES

Tablets were made containing ingredients per tablet as shown below. In each case, the ingredients were weighed out in the proportions shown, the ingredients were mixed together, and the mixed powder was made into tablets on a table press. The quantities shown are mg per tablet.

|  | #1 | #2 | #3 | #4 | #5 | #6 |
|---|---|---|---|---|---|---|
| Enalapril Maleate | 20.0 | 20.0 | 20.0 | 20.0 | 20.0 | 5.0 |
| Lactose Monohydrate |  | 150. | 157. | X | X | X | X |
| Lactose Anhydrous |  | X | X | 157. | X | X | 165. |
| Dextrates | X | X | X | 157. | X | X |  |
| Compressible Sugar |  | X | X | X | X | 157. | X |
| Iron Oxides | 0.5 | 0.5 | 0.5 | 0.5 | 0.5 | X |  |
| Stearic Acid | 7.0 | X | X | X | X | X |  |
| Zinc Stearate |  | X | 2.5 | 2.5 | 2.5 | 2.5 | X |
| Glyceryl Monostearate |  | X | X | X | X | X | 10.0 |
| Colloidal Sillicon Dioxide | 2.5 | X | X | ·X | X | X |  |
| TOTAL: | 180 | 180 | 180 | 180 | 180 | 180 |

For all of examples 1 to 6, the extent of decomposition was found to be less than one percent after storage of the tablets at 50° C. for 2 weeks.

What is claimed is:

1. A stable solid pharmaceutical composition comprising enalapril maleate and a carrier, wherein said carrier is free or substantially free of microcrystalline cellulose, cellulose derivatives or cellulose polymers and calcium phosphate and free or substantially free of disintegrant, at least fifty percent by weight of the carrier consists of one or more pharmaceutically acceptable water-soluble substances not being cellulose derivatives or cellulose polymers; and the carrier is substantially free of magnesium stearate and includes a lubricant which is other than magnesium stearate.

2. A composition as in claim 1 wherein a water-soluble substance is a carbohydrate.

3. A composition as in claim 1 wherein a water soluble-substance is selected from the group consisting of lactose monohydrate, lactose anhydrous, dextrates, dextrose, dextrin, compressible sugar, mannitol and sorbitol.

4. A composition as in claim 1 wherein a water soluble substance is lactose monohydrate or lactose anhydrous.

5. A composition as in claim 1 wherein the lubricant is stearic acid.

6. A composition as in claim 1 wherein the lubricant is a salt or ester of stearate acid which is other than magnesium stearate or calcium stearate.

7. A composition as in claim 1 wherein the lubricant is zinc stearate.

8. A composition as in claim 1 wherein the lubricant is glyceryl monostearate.

9. A composition as in claim 1 wherein the water-soluble substance or substances comprise at least eighty percent of the carrier by weight.

10. A composition as in claim 1 wherein the water-soluble substance or substances comprise t least ninety-five percent of the carrier by weight.

11. A stable solid pharmaceutical composition comprising enalapril maleate and a carrier, said carrier being free or substantially free of microcrystalline cellulose and free or substantially free of disintegrant, wherein at least fifty percent by weight of the carrier consists of one or more pharmaceutically acceptable water-soluble substances; and the carrier is substantially free of magnesium stearate and includes a lubricant which is other than magnesium stearate.

\* \* \* \* \*